US012616717B2

(12) United States Patent
Tornatore

(10) Patent No.: US 12,616,717 B2
(45) Date of Patent: May 5, 2026

(54) REGENERATIVE CO₂ TREATMENT APPARATUS AND METHOD

(71) Applicant: Renee Tornatore, Corydon, IN (US)

(72) Inventor: Renee Tornatore, Corydon, IN (US)

( * ) Notice: Subject to any disclaimer, the term of this patent is extended or adjusted under 35 U.S.C. 154(b) by 0 days.

(21) Appl. No.: 16/924,873

(22) Filed: Jul. 9, 2020

(65) Prior Publication Data

US 2021/0008102 A1 Jan. 14, 2021

Related U.S. Application Data

(60) Provisional application No. 62/872,749, filed on Jul. 11, 2019.

(51) Int. Cl.
| | |
|---|---|
| *A61K 33/00* | (2006.01) |
| *A61K 9/00* | (2006.01) |
| *A61K 9/46* | (2006.01) |
| *A61N 1/32* | (2006.01) |
| *A61N 1/36* | (2006.01) |
| *A61N 1/38* | (2006.01) |

(52) U.S. Cl.
CPC ............ *A61K 33/00* (2013.01); *A61K 9/0007* (2013.01); *A61K 9/0014* (2013.01); *A61N 1/326* (2013.01); *A61N 1/36014* (2013.01); *A61N 1/38* (2013.01)

(58) Field of Classification Search
CPC .... A61K 33/00; A61K 9/0014; A61K 9/0019; A61K 2800/87; A61K 9/0007
See application file for complete search history.

(56) References Cited

U.S. PATENT DOCUMENTS

| | | | |
|---|---|---|---|
| 2004/0081642 A1 | 4/2004 | Loscalzo et al. | |
| 2007/0016117 A1 | 1/2007 | Sliwa | |
| 2017/0246205 A1* | 8/2017 | Stasko ................... | A61K 33/00 |
| 2021/0008102 A1 | 1/2021 | Tornatore | |

FOREIGN PATENT DOCUMENTS

| | | | | |
|---|---|---|---|---|
| WO | WO2014142970 A9 * | 9/2014 | ............ | A61M 37/00 |

OTHER PUBLICATIONS

Apec Water, Free Carbon Dioxide in Water, downloaded in Sep. 2021 (Year: 2021).*
Pietro Romeo, Extracorporeal Shock Wave Therapy in Musculo-skeletal Disorders: A Review, Med Princ Pract 2014;23:7-13 (Year: 2014).*
Luther C. Kloth, Electrical Stimulation Technologies for Wound Healing, Advances in Wound Care, vol. 3, No. 2, 2014 (Year: 2014).*
Alu Bohuslavs'kyï, Effect of nitric oxide on the efficiency of oxygen consumption by the working skeletal muscle in fatigue]. Fiziol Zh. 2005;51(1):33-42. Ukrainian. PMID: 15801198 (Year: 2005).*

Research-Gate, "A simplified version of the mTOR signalling pathway," article (May 4, 2020) 14 pages, https://www.researchgate.net/figure/A-simplified-version-of . . . thway-MTORC1-received-and-integrates-the_fig1_257103989.
Levin, "Molecular Bioelectricity: how endogenous voltage potentials control cell behavior and instruct pattern regulation in vivo," article (Dec. 1, 2014) Molecular Biology of the Cell Perspective, vol. 25, pp. 3835-3850.
The American Society for Cell Biology, "Molecular Biology of the Cell Chart (MBoC)," article (Dec. 1, 2014) 2 pages, https://www.ncbi.nim.nih.gov/pmc/articles/PMC4244194/figure/F1/.
Kumar et al., "Hypoxia Inducible Factor pathway and Physiological Adaptation: A Cell Surbival Pathway?," article (Sep. 27, 2015) pp. 1-22, Department of Biotechnology, Konkuk University, https://www.ncbi.nim.nih.gov/pmc/articles/PMC4600544/.
Tyler, "Nature's Electric Potential: A Systematic Review of the Role of Bioelectricity in Wound Healing and Regenerative Processes in Animals, Humans, and Plants," article (Sep. 4, 2017) vol. 8, Article 627, 18 pages, Frontiers in Physiology, www.frontiersin.org.
Blanpain et al., "Epithelial Stem Cells: Turning over New Leaves," article (Feb. 9, 2007) 26 pages, https://www.ncbi.nlm.nih.gov/pmc/articles/PMC2408375/.
Ledford, "Electric switch could turn on limb regeneration," article (Feb. 28, 2007) 4 pages, https://www.nature.com/news/2007/070226/full/news070226-8.html.
Oliveira, et al., "Electrical stimulation shifts healing/scarring towards regeneration in a rat limb amputation model," article (Aug. 7, 2019) 14 pages, Scientific Reports, (2019)9:11433, https://doi.org/10.1038/s41598-19-47389-w.
Atala, et al., "Wound Healing Versus Regeneration: Role of the Tissue Environment in Regenerative Medicine," article (Jan. 1, 2011) 24 pages, Howard Hughes Medical Institute, https://www.ncbi.nlm.nih.gov/pmc/articles/PMC3826556/.
Tseng, et al., "Cracking the bioelectric code; Probing endogenous ionic controls of pattern formation," article (Jan./Feb. 2013) Communicative & Integrative Biology, vol. 6, Issue 1, p. 1-8, www.landesbioscience.com.
Choudhry, et al., "Advances in Hypoxia-Inducible Factor Biology," article (Feb. 6, 2018) Cell Metabolism 27, pp. 281-298, https://doi.org/10.1016/j.cmet.2017.10.005.
Preston, "Salamander's Genome Guards Secrets of limb Regrowth," article (Jul. 2, 2018) 13 pages, Developmental Biology, https://www.quantmagazine.org/axolotl-genome-slowly-yields-secrets-of-limb-regrowth-20180702/.
Paddock, "Study shows blood cells need nitric oxide to deliver oxygen," article (Apr. 13, 2015) 2 pages, Medical News Today, https://www.medicalnewstoday.com/articles/292292.php.

(Continued)

*Primary Examiner* — Mark V Stevens
(74) *Attorney, Agent, or Firm* — Amundsen Davis, LLC

(57) ABSTRACT

The present technology provides regenerative treatment methods and apparatus to promote regeneration of target biological tissue. Regenerative treatments include the subcutaneous and cutaneous application of carbon dioxide. Regenerative treatment methods include an initial treatment phase and a maintenance treatment phase. Regenerative treatment apparatus include effervescent mineral compositions for cutaneous application of carbon dioxide.

19 Claims, 5 Drawing Sheets

(56) References Cited

OTHER PUBLICATIONS

Wei, et al., "Roles of mTOR Signaling in Tissue Regeneration," article (Sep. 12, 2019) 25 pages, https://www.ncbi.nlm.nih.gov/articles/PMC6769890/.

Nagoba, "Role of Acid in Wound Healing," article (Apr. 30, 2020) 6 pages, https://www.woundresearch.com/article/acidic-environment-and-wound-healing-review.

Ultima Neuro, "Stimulator Info," article, (Jul. 22, 2015) 6 pages.

Buarque De Gusmao, et al., "Advanced Techniques in Bone Regeneration," article (Aug. 31, 2016) 19 pages, DOI: 10.5772/63745, https://www.intechopen.com/books/advanced-techniques-in-bon . . . ion/acoustic-therapy-as-mechanical-stimulation-of-osteogenesis.

Kumar et al., "Adult skin-derived precursor Schwann cells exhibit superior myelination and regeneration supportive properties compared to chronically denervated nerve-derived Schwann cells," article (2016) 2 pages, https://www.ncbi.nlm.nlh.gov/m/pubmed/26854934/?=4&/rom=/2440805/related.

McLaughlin, et al., "Bioelectric signaling in regeneration: Mechanisms of ionic controls of growth and form," article (Dec. 25, 2017) 13 pages, Developmental Biology 433 (2018) 177-189, https://dx.doi.org/10.1016/j.ydbio.2017.08.032.

Zelenkova, "Carboxytherapy Non-Invasive Method in Dermatology and Some Other Branches of Medicine," article (Apr. 8, 2019) ACTA Scientific Medical Sciences, vol. 3, Issue 5, May 2019, pp. 42-48.

Sakai, et al., "A Novel System for Transcutaneous Application of Carbon Dioxide Causing an "Artificial Bohr Effect" in the Human Body," article (2011) 2 pages, Plos One, https://journals.plos.org/plosone/article?id=10.1371/journal.pone0024137.

Greijer Ae, et al., "Up-regulation of gene expression by hypoxia is mediated predominantly by hypoxia-inducible factor 1 (HIF-1)," article (2005) 2 pages, https://www.ncbi.nlm.nih.gov/m/pubmed/15906272/.

Li et al., "Exposure to 50 Hz electromagnetic fields enhances hair follicle regrowth in C57BL/6 mice" article (2019) Experimental Biology and Medicine (Maywood) 244(5): pp. 389-394, https://www.ncbi.nlm.nih.gov/pmc/articles/PMC6488868/.

Schleip et al., "Fascia Is Able to Actively Contract and May Thereby Influence Musculoskeletal Dynamics: A Histochemical and Mechanographic Investigation | Physiology" article (2019) Frontiers in Physiology, pp. 1-15 https://doi.org/10.3389/fphys.2019.00336.

Stem-Rim, "What is Regeneration-inducing Medicine?," article (2022) 3 pages, https://stemrim.com/english/about/theirs/.

Uppsala University, "Nitric oxide a possible treatment for COVID-19, study finds," article (2020) 3 pages, https://www.sciencedaily.com/releases/2020/10/201002111724.htm.

Tejero et al., "Sources of Vascular Nitric Oxide and Reactive Oxygen Species and Their Regulation," article (2018) Physiol Rev 99: pp. 311-345, https://journals.physiology.org/doi/pdf/10.1152/physrev.00036.2017.

TMD—Occlusion, "Hair Loss: The Real Underlying Causes Are Not Androgenetic," article (2020) 14 pages, https://tmdocclusion.com/home/connection-to-other-diseases-and-syndromes/hair-loss/.

Tellez-Segura, "Involvement of Mechanical Stress in Androgenetic Alopecia," article (2015) International Journal of Trichology: 7(3), PMC4639964, pp. 95-99, https://www.ncbi.nlm.nih.gov/pmc/articles/PMC4639964/.

Gao et al., "Correlation between cervical lordosis and cervical disc hern . . . : Medicine," article (2019) Medicine: vol. 98, Issue 31, pp. 1-6, https://journals.lww.com/md-journal/fulltext/2019/08020/correlation_between_cervical_lordosis_and_cervical.15.aspx.

Shin et al., "Temporal Trends in Cervical Spine Curvature of South Korean Adults Assessed by Deep Learning System Segmentation, 2006-2018," article (Oct. 15, 2020) pp. 1-13, JAMA Network Open, https://jamanetwork.com/journals/jamanetworkopen/fullarticle/2771734.

Homer Nazeran et al, Nanoscale Glutathione Patches Improve Organ Function, SBEC 2010, IFMBE Proceedings 32, pp. 134-137, 2010 (Year 2010).

Air Pollution Information System, Nitrogen Oxides (NOx), Air Pollution Information System, downloaded in Aug. 2024 (Year 2024).

Rafet Koca et al., Evaluation of lipid peroxidation, oxidant/antioxidant status, and serum nitric oxide levels in alopecia areata, Med Sci Monit, 2005, 11(6): CR296-299 (Year 2005).

Kjean, Rotator Cuff Surgery—4 weeks post-op, p. 8, Shoulder Problems, Forums, Patient, publication date 2016 (Year 2016).

Tejero et al., "Sources of Vascular Nitric Oxide and Reactive Oxygen Species and Their Regulation," article (2018) Physiol Rev 99: pp. 346-379, https://journals.physiology.org/doi/pdf/10.1152/physrev.00036.2017.

* cited by examiner

REGENERATIVE CO₂ TREATMENT APPARATUS AND METHOD

RELATED APPLICATIONS

This application claims the benefit of U.S. Provisional Application No. 62/872,749, entitled "CO2 Treatment Apparatus and Method," filed Jul. 11, 2019, and the disclosure thereof is hereby incorporated by reference in its entirety.

FIELD OF THE INVENTION

The present technology relates to the use of carbon dioxide ($CO_2$) for regenerative therapeutic purposes, and provides certain methods of regeneration treatment, as well as devices for implementing treatment and for the delivery of carbon dioxide to targeted body tissues.

BACKGROUND

The regeneration of damaged biological tissues is of significant interest. Regeneration is distinguishable from processes of scarring and healing, and regenerative medicine focuses on ways to optimize tissue regeneration by therapeutically manipulating the body's natural reaction of fibroblast deposition and scar formation in response to injury or disease. Various strategies have been developed for regenerative treatments to promote tissue regeneration, including for example, the use of biomaterials as scaffolds, cells, and combinations of biomaterials and cells.

Many studies have been conducted in both plants and animals to try to understand how regenerative processes work. For example, as described in "Nature's Electric Potential: A systematic Review of the Role of Bioelectricity in Wound Healing and Regenerative Process in Animals, Humans, and Plants, from the Frontiers in Physiology," Shena E. B. Tyler (Frontiers in Physiology, Sep. 4, 2017), regenerative processes can be broken down into five phases.

In the first phase, there is an injury (wound), or disruption to the tissue cells, such as by 1) spatial variations in ion channels or pumps, or 2) disruption in gap junctions. This creates extracellular ionic current flow, and established voltage gradients. This essentially creates a bioelectric voltage gradient. Bioelectricity is the flow of current carried by mobile charged ions, across cell membrane and along exterior and interior ionic environments of cells. The body then responds by initiating processes to either regenerate or scar and repair.

In the second phase, changes in polarity are communicated. The signals may be carried via: Electrical Fields— presence of dipole with no immediate barrier; Membrane potential—presence of dipole across barrier with selective permeability created by ion gradients across a membrane via action of ion channels and pumps; Flux—flow of ions through channels or pumps per unit of time; PH gradients— by proton pumps to modify H+ gradients. The article "Bioelectric Signaling in Regeneration: Mechanisms of Ionic Controls of Growth and Form," McLaughlin et al., (Developmental Biology 433 (2018)), explains that transmembrane potentials, fluxes of individual ions, and iso-electric cell compartments that are established by gap junctions, convey information to at least target cells. Further, as described in the article "Molecular Bioelectricity: How Endogenous Voltage Potentials Control Cell Behavior And Instruct Pattern Regulation in Vivo," Michael Levin (Molecular Biology of the Cell, Dec. 1, 2014), it is believed that this signaling modality is used to process and transmit information about regenerative parameters such as cell type, tissue size, positional information, axial polarity, and organ identity.

The third phase involves mechanisms acting as receptors for the signals, such as proton pumps and other cells. Biophysical transduction mechanisms may include: 1) Voltage sensing domain, 2) loss of intracellular K+, Electroosmosis 4) Voltage gating of signaling molecular transport, 5) Ca++ influx, 6). Secondary response, amplification, transcriptional effectors may include: 1) integrin, 2) Slug/Sox10, 3) Notch, 4) NF-kB, 5) PTEN.

The fourth phase includes ionic flux, which involves the downstream activation of a number of gene responses, which evoke transcriptional cascades involved in the control of morphologies and regeneration.

The fifth phase involves initiating a cascade of events through cellular death and proliferation, and differentiation of stem cells to regenerate parts, pieces, or entire modules. It is believed that when bioelectric patterns are specifically disrupted, predictable and coherent changes in morphogenesis occur. It is also believed that the necessary parameter is voltage potential, without regard necessarily to any one channel gene (which could have had scaffold or binding roles) or even any one ion type (which could have had chemical, not electrical, roles). Accordingly, achieving the correct voltage in the target biological tissue may trigger the regenerative cascade to regenerate parts, pieces, or entire modules.

One example of a treatment that has been developed for use regenerative therapies in humans is carboxytherapy. Typically, carboxytherapy uses a series of small injections with a thin needle attached to a tube which delivers tiny quantities of medical grade carbon dioxide below the skin's surface in a controlled flow and dose via a specially designed machine.

Carbon dioxide acts as a signal for poor blood circulation in the body. For example, when a human inhales, they breathe in oxygen into the lungs, and red blood cells pick up that oxygen and carry it to tissues in the body. Tissue cells within the body release carbon dioxide as their waste product. When blood cells encounter high concentrations of carbon dioxide, they release oxygen molecules they are carrying and pick up the carbon dioxide, carrying it back to the lungs to be exhaled. The article "Carboxytherapy Non-Invasive Method in Dermatology and Some other Branches of Medicine," Zelenkova (ATCA 3:5 2019) describes carboxytherapy and effects it has on the human body, including the Bohr effect and that an increase in blood $CO_2$ concentration leads to a decrease in blood pH, which will result in hemoglobin proteins releasing their load of oxygen, while, conversely a decrease in blood $CO_2$ provokes an increase in pH, which results in hemoglobin picking up more oxygen.

It has been found that when small amounts of carbon dioxide gas are injected just below the surface of the skin, the body reacts by increasing the blood circulation to that area. Studies have demonstrated that carboxytherapy improves skin elasticity, improves circulation, encourages collagen repair, improves the appearance of fine lines and wrinkles, and destroys localized fatty deposits. The most common aesthetic indications for treatment with carboxytherapy are for cellulite and localized fat reduction, stretch marks (striae), acne scars, skin laxity and wrinkle reduction.

However, it is believed that carboxytherapy alone does not utilize all five phases of the regenerative processes discussed above. Accordingly, it is desirable to provide improved regenerative treatments.

SUMMARY OF THE INVENTION

The present technology provides regenerative treatment methods and apparatus to promote regeneration of target biological tissue using subcutaneous and cutaneous application of carbon dioxide.

In one example, a regenerative treatment method for treating target biological tissue within a target area of a patient is provided. The method includes an initial treatment phase and a maintenance treatment phase. The initial treatment phase includes at least one initial phase therapy session and at least one initial phase personal administration, wherein each initial phase therapy session includes at least subcutaneous application of carbon dioxide in the target area and each initial phase personal administration includes at least cutaneous application of carbon dioxide to the target area. The maintenance treatment phase occurs after the initial treatment phase, and includes at least one maintenance phase therapy session and at least one maintenance phase personal administration, wherein each maintenance phase therapy session includes at least subcutaneous application of carbon dioxide in the target area and each maintenance phase personal administration includes at least cutaneous application of carbon dioxide to the target area.

In another example, effervescent mineral compositions for the cutaneous application of carbon dioxide to a target area of a patient are provided. The effervescent mineral compositions include at least bicarbonate, acid, and at least one fat facilitator.

In a third example, a regenerative treatment apparatus for providing regenerative treatment to a target area including target biological tissue of a patient is provided. The regenerative treatment apparatus includes a first water bath and a second water bath, each water bath containing a volume of water and an effervescent mineral composition. The regenerative treatment apparatus also includes an electrical stimulator comprising a current generator, a positive lead connected to the current generator, and a negative lead connected to the current generator, the positive lead being further connected to the first water bath, and the negative lead being further connected to the second water bath.

BRIEF DESCRIPTION OF THE DRAWINGS

Specific examples have been chosen for purposes of illustration and description, and are shown in the accompanying drawings, forming a part of the specification. Like components within the drawings are given the same reference numbers.

DETAILED DESCRIPTION

Regenerative treatment methods of the present technology may be used to treat biological tissue damage and/or deterioration. Examples of biological tissue damage include, for example, damage caused by neuromuscular skeletal (NMSK) conditions, or by lack of circulation, which can result in physical and aesthetic deterioration. Poor circulation of blood results in a poor supply of oxygen, which leads to deterioration of bodily tissues, since such tissues rely upon oxygen to remain intact and healthy. When body tissues are stressed or damaged, they often experience inflammation. Repeated inflammation over time can cause a buildup of scar tissue, which is poorly vascularized. Lack of blood flow to poorly vascularized areas can cause deterioration of and further damage to the biological tissue. Conditions that result can include physical damage such as neuropathy, or arthritic joints, and aesthetic damage such as imperfections such as dark under-eye circles, scarring and cellulite.

Regenerative treatments methods of the present technology may be used to treat physical or aesthetic damage to patient biological tissues. Regenerative treatment methods of the present technology may be performed on any target area containing target biological tissue of the patient's body, including for example the face, neck, arms, feet, knees, hands, abdomen thighs, and fascia. As used herein, the target area includes the target biological tissue, as well as the external and internal areas of the patient's body immediately surrounding the target biological tissue within inches. For example, if the target biological tissue is located within the knee, the target area includes the entirety of the knee as well as areas immediately surrounding the knee within inches.

Regenerative treatment methods of the present technology include a combination of subcutaneous and cutaneous applications of carbon dioxide. At least the subcutaneous application of carbon dioxide is administered during therapy sessions, in a clinical setting. Some cutaneous applications of carbon dioxide may occur during therapy sessions, and some may be personally administered, by the patient or a caregiver, outside the clinical setting, such as at home.

Figure 1:
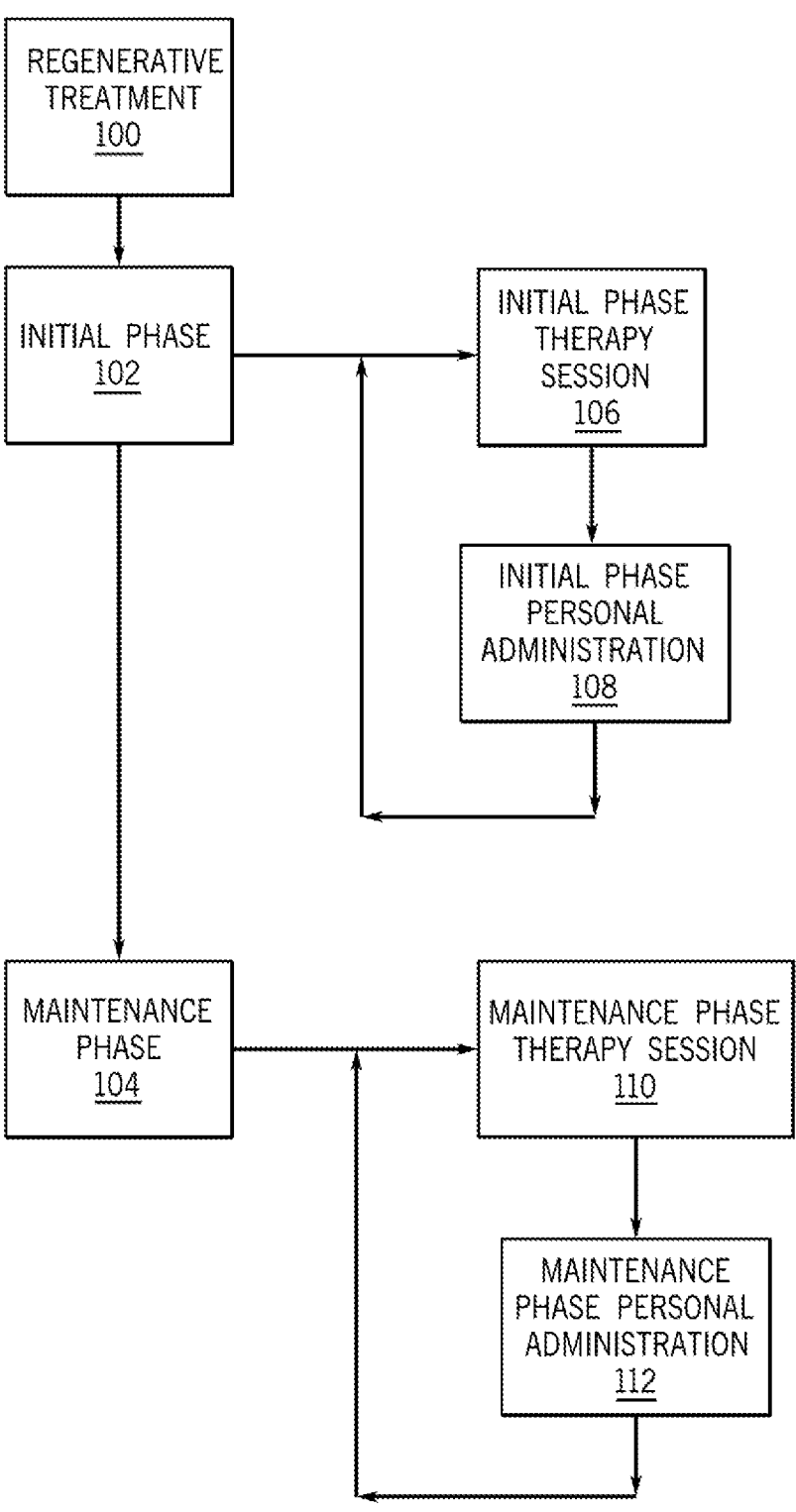
FIG. 1 is a flow chart illustrating one example of a regenerative treatment method of the present technology.

As shown in FIG. 1, a regenerative treatment method 100 of the present technology includes two treatment phases: an initial treatment phase at step 102, and a maintenance treatment phase at step 104. Generally, the initial treatment phase 102 includes at least one initial phase therapy session at step 106, and may also include at least one initial phase personal administration session at step 108. The initial phase 102 generally includes a pre-determined number of repetitions of at least step 106, and thus a pre-determined number of initial phase therapy sessions. The initial phase therapy sessions at step 106 tend to be administered in relatively close proximity in time, and are intended to regenerate target biological tissue. The initial phase 102 also generally includes a plurality of initial phase personal administrations at step 108. Steps 106 and 108 may be carried out in succession and that succession may be repeated a set number of times. Alternatively, during the initial phase 102, either of initial phase therapy session at step 106 or the initial phase personal administrations at step 108 may be repeated prior to any further occurrence of the other step. Preferably, the initial phase 102 includes at least one initial phase therapy session at step 106, and also includes at least one initial phase personal administration session at step 108 that occurs after the at least one initial phase therapy session at step 106.

The maintenance phase at step 104 includes at least one maintenance phase therapy session at step 110, and may also include at least one maintenance phase personal administration 112, as well as repetitions of each step as desired or recommended. The repetitions of step 110 maintenance phase therapy session may be spaced father apart in time than the initial phase therapy sessions at step 106, and are intended to at least maintain the level of regeneration achieved during the initial treatment phase at step 102. The number of maintenance phase therapy sessions 110 may be indefinite, and may be periodic continuously for any suitable period of time, up to and including the lifetime of the patient. Steps 110 and 112 may be carried out in succession and that succession may be repeated a set number of times. Alternatively, during the maintenance phase 104, either of maintenance phase therapy session at step 110 or the maintenance phase personal administrations at step 112 may be repeated prior to any further occurrence of the other step. Preferably, the maintenance phase 104 includes at least one maintenance phase therapy session at step 110, and also includes at least one maintenance phase personal administration session at step 112 that occurs after the at least one maintenance phase therapy session at step 112.

The number of initial phase therapy sessions 106 may vary from patient to patient, or based upon the type of damage intended to be treated. The number of initial phase therapy sessions 106 may be any suitable number of therapy sessions, such as from six to twenty therapy sessions. In some instances, the number of initial phase therapy sessions 106 may be less than six, or greater than twenty. In other examples, the number of initial phase therapy sessions 106 may be, for example, six, seven, eight, nine, ten, eleven, twelve, thirteen, fourteen, fifteen, sixteen, seventeen, eighteen, nineteen, or twenty.

The frequency of initial phase therapy sessions 106 may also vary from patient to patient, or based upon the type of damage intended to be treated. During the initial treatment phase 102, initial phase therapy sessions 106 are preferably scheduled to occur multiple times per week, such as every other day, or spaced in time such that there are two or three days between each initial phase therapy session 106. In some examples, the frequency of initial phase therapy sessions 106 may be two, three, or four per week during the initial treatment phase 102.

The maintenance phase 104 of regenerative treatment method 100 is intended to be long term, potentially indefinite. The maintenance phase 104 may include maintenance phase therapy sessions at step 110, which may be spaced apart over a greater periods of time than the initial phase therapy sessions at step 106. For example, during the maintenance phase 104, the step of a maintenance phase therapy session 110 may be performed once per month, or once every two months. In addition, or alternatively, to therapy sessions, the maintenance phase 104 may include maintenance phase personal administration of cutaneous carbon dioxide at step 112. Maintenance phase personal administration 112 of cutaneous carbon dioxide may occur more frequently than therapy sessions 110 during the maintenance phase 104, such as once per week, or even as needed.

Figure 2:
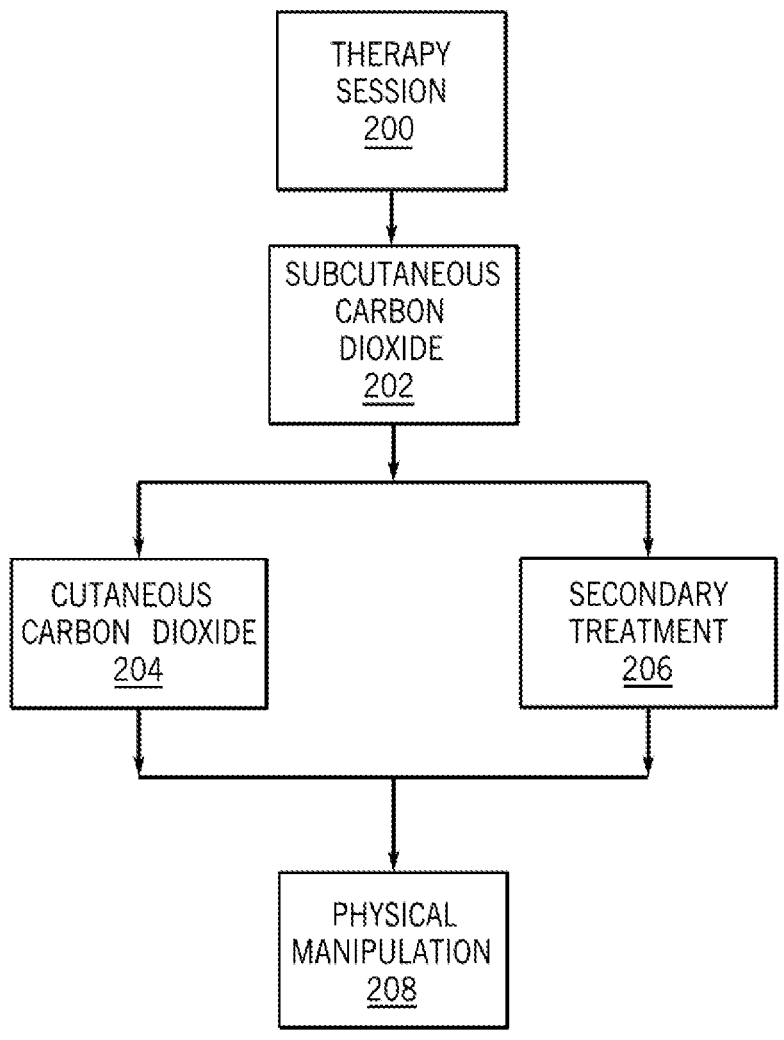
FIG. 2 is a flow chart illustrating on example of a therapy session of the regenerative treatment method of FIG. 1.

FIG. 2 illustrates one example of a therapy session 200 of the present technology, which may be an initial phase therapy session 106 or a maintenance phase therapy session 110.

Each therapy session 200 of the present technology includes at least one subcutaneous application of carbon dioxide at step 202. Subcutaneous application of carbon dioxide is administered by a clinician, and the carbon dioxide is injected in at least one location within the target area. Without being bound by any particular theory, injection of carbon dioxide is believed to provide many benefits, including potentially ripping scar tissue, stimulating blood flow, and promoting collagen formation. Injection of carbon dioxide may create a positive electrical event, and the carbon dioxide may disrupt all cells in the whole plane into which it is injected, causing an ionic gradient from resting to positive. With reference to phase 1 of the regenerative processes discussed above, injection of carbon dioxide may cause injury of cells so that the target biological tissue can regenerate new cells. Injection of carbon dioxide may initiate a downstream cascade of events via HIF (hypoxia induced factor) via the mTOR pathway as well as other pathways. With reference to phase 2 of the regenerative processes discussed above, injection of carbon dioxide may cause changes in the gap junction, which may initiate electrical field and membrane potential changes. Injection of carbon dioxide may also induce ionic flux and PHgradient changes due to the H+ characteristic of the $CO_2$ molecules in the carbon dioxide gas.

Each therapy session 200 may also include steps that are intended to cause or promote the third, fourth, and fifth phases of the regenerative process described above. Without being bound by any particular theory, it is believed that the subcutaneous application of carbon dioxide causes a wound, and initiates the first and second phases of the regenerative process. The carbon dioxide also serves as an anti-inflammatory, which may reduce the likelihood that the body will produce scar tissue, and thus facilitate the promotion of tissue regeneration. Regenerative treatments of the present technology take advantage of the presence of the subcutaneous carbon dioxide, and use the additional therapy steps described below to promote tissue regeneration.

For example, each therapy session 200 may include cutaneous application of carbon dioxide to the target area at step 204. Because a patient's skin is porous and permeable, applying carbon dioxide to the outer surface of the skin is believed to promote circulation and encourage blood flow towards the upper membrane of the skin in the application area. Without being bound by any particular theory, this may cause electrophoretic movement of signaling molecules through gap junctions. It is believed that the cutaneous application of carbon dioxide may also promote the Bohr Effect, and induces gap junction disturbance, enhances oxygen concentrating at the target biological tissue, and increases electrical conductivity in the target biological tissue area.

Depending upon the type of tissue damage a patient has, each therapy session 200 of the present technology may include application of a secondary treatment to the target area at step 206. The secondary treatment may be applied instead of, simultaneously with, or subsequent to the cutaneous application of carbon dioxide of step 204. Without being bound by any particular theory, secondary treatments of the present technology may cause or promote ionic flux, and flipping positive and negative polarities within the target biological tissue. Either alone, or in combination with application of carbon dioxide to the target area at step 204, secondary treatment at step 206 may trigger a regenerative cascade within the target biological tissue.

In a first example, such as when the biological tissue damage or deterioration is caused by neuropathy, the secondary treatment at step 206 may be the application of electrical stimulation to the target area. The electrical stimulation includes the creation of an electrical pathway, where current runs through a loop that includes at least the target area of the patient. For example, a patient may sit with each foot placed in a separate water bath, and an electrical circuit may be established with one lead connecting to a first water bath containing the first foot of the patient and a second lead connected to the second water bath containing the second foot of the patient. The patient thus forms a link in the circuit, and when current is run through the circuit, it travels through at least the legs of the patient.

Figure 3:
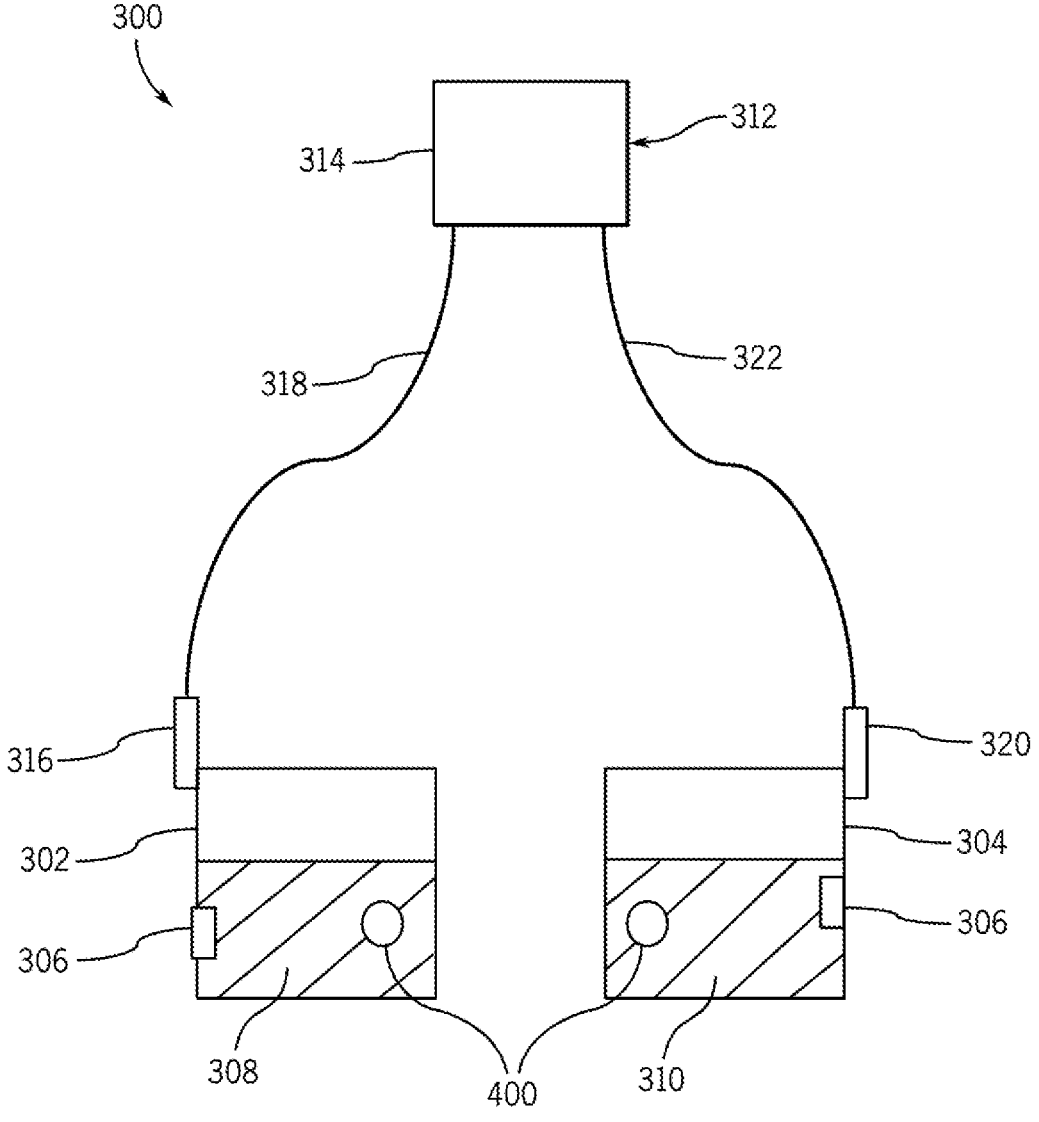
FIG. 3 illustrates one example of a regenerative treatment apparatus of the present technology.

FIG. 3 illustrates a regenerative treatment apparatus 300 for use in a regenerative treatment in which the secondary treatment at step 206 is be the application of electrical stimulation. Regenerative treatment methods of the present technology that include the simultaneous cutaneous administration of carbon dioxide to and electrical stimulation of the target area may include using a regenerative treatment apparatus 300.

The regenerative treatment apparatus 300 includes a first water bath 302, and a second water bath 304. The first and second water baths 302, 304 are each configured, with respect to size and shape, to receive one foot of a patient. Preferably, the first and second water baths 302, 304 are each configured, with respect to size and shape, to receive one foot of a patient while the patient is in a seated position. The first water bath 302 and the second water bath 304 may each contain at least one water movement generator 306, such as a fan, blower, jet, or other suitable device configured to create movement of the water within the water bath. The first water bath 302 may contain a first volume of water 308, and the second water bath 404 may contain a second volume of water 310. The volume of water in each water bath is preferably deep enough to cover that patient's foot to at least mid ankle, and is preferably at a temperature that is comfortably warm for the patient.

During regenerative treatment, the first water bath 302 and the second water bath 304 may each contain an effervescent mineral composition 400. Examples of suitable effervescent mineral compositions for use as effervescent mineral composition 400 are described more fully below, in reference to FIG. 4. While the effervescent mineral composition 400 in each water bath is illustrated as being in a sphere, it can be in any form, including tablet or powder. It should be understood that once added to the volume of water in the water bath, the effervescent mineral composition 400 will lose its original form, and at least some components thereof may form a solution with the volume of water. Further, upon contact with the water in the water bath, components of the effervescent mineral composition 400 will activate, causing the formation of carbon dioxide bubbles within the water bath, and causing cutaneous application of carbon dioxide to any target biological tissue in contact with the water bath.

The regenerative treatment apparatus 300 may also include a nerve stimulator 312. The electrical stimulator 312 includes a current generator 314, a positive lead 316 connected to the current generator 314 by a first wire 318, and a negative lead 320 connected to the current generator 314 by a second wire 322. The current generator 314 may be configured to generate biphasic current with frequency of 8 Hertz and a voltage of +0 to 36V, and –0 to 36V. The current generator 314 may be further configured to generate current having a symmetrical biphasic rectangular wave form that modulates with bursts every 5 seconds on and off. The positive lead 316 may be connected to the first water bath 302, and the negative lead 320 may be connected to the second water bath 304.

Regenerative treatment methods of the present technology using a regenerative treatment apparatus 300 may include providing a first water bath 302 and a second water bath 304, where each water bath contain a volume of water 308, 310, and an effervescent mineral composition 400. The effervescent mineral composition 400 in each water bath will be activated by the water, generating carbon dioxide bubbles and thus providing cutaneous application of carbon dioxide to any target area in contact with the water.

Regenerative treatment methods of the present technology using a regenerative treatment apparatus 300 may also include providing an electrical stimulator 312. The electrical stimulator 312 may include a current generator 314 having a positive lead 316 connected to the current generator 314 and a negative lead 320 connected to the current generator 314. The positive lead 316 may also be connected to the first water bath 302, and the negative lead 320 may be connected to the second water bath 304. The method may include providing electrical stimulation using the electrical stimulator, by generating a biphasic current using the current generator.

When the secondary treatment step 206 of regenerative treatment method 100 is electrical stimulation, the electrical stimulation may be applied to at least the target area for a period of time. The period of time may be any suitable period of time, such as a period of time from about 5 minutes to about 60 minutes, or from about 10 minutes to about 30 minutes, including for example about 5 minutes, about 10 minutes, about 15 minutes, about 20 minutes, about 25 minutes, 30 minutes, or more.

In a second example, such as when the biological tissue damage or deterioration is caused by a neuromuscular skeletal condition, the secondary treatment at step 206 may be electrical stimulation, such as described above or the application of extracorporeal shock wave therapy (ESWT) to the target area using an extracorporeal shock wave therapy machine (not shown). The parameters for any application of extracorporeal shock wave therapy may vary based upon the condition being treated. For example, when the condition is planar fasciitis in the shoulder, the extracorporeal shock wave therapy may be applied at 12 Hz for 1500 pulses. When the condition is in a patient's knee, the extracorporeal shock wave therapy may be applied at 15 hz for 2000 pulses. When the condition is erectile dysfunction the extracorporeal shock wave therapy may be applied at 10 hz for 1200 pulses. When the condition is in a patient's spine, including for example neck pain, and back pain, the extracorporeal shock wave therapy may be applied at 10 hz for 20000 pulses. Without being bound by any particular theory, it is believed that extracorporeal shock wave therapy creates electric potentials, and may induce transient cell membrane hyperpolarization. The application of extracorporeal shock wave therapy tends to reduce inflammation in the target biological tissue, which may restore range of motion and function.

Referring back to FIG. 2, each therapy session 200 may also include physical manipulation 208 of at least the target area. Physical manipulation preferably occurs subsequent to the subcutaneous application of carbon dioxide at step 202. Physical manipulation preferably also occurs subsequent to the subcutaneous application of carbon dioxide at step 202, the secondary treatment of step 206, or both the subcutaneous application of carbon dioxide at step 202 and the secondary treatment of step 206. Physical manipulation is intended to increase range of motion to the target area of the patient. For example, patients who have neuropathy often experience loss of range of motion, in addition to loss of circulation, in extremities such as feet and hands, which may benefit from physical manipulation.

Referring back to FIG. 1, the initial phase personal administration at step 108 and the maintenance phase personal administration at step 112 each include administration of cutaneous carbon dioxide to at least the target area. The patient, or a caretaker, may administer cutaneous carbon dioxide at least once or twice per week, or more frequently. The cutaneous carbon dioxide may be administered on the same day as, prior to or after, a scheduled therapy session, or on days when a therapy session is not scheduled. The administration of cutaneous carbon dioxide may include using effervescent mineral compositions of the present technology. Effervescent mineral compositions 400 of the present technology may be provided in any suitable form, including for example a bath additive, tablet, or enclosed pack.

Figure 4:
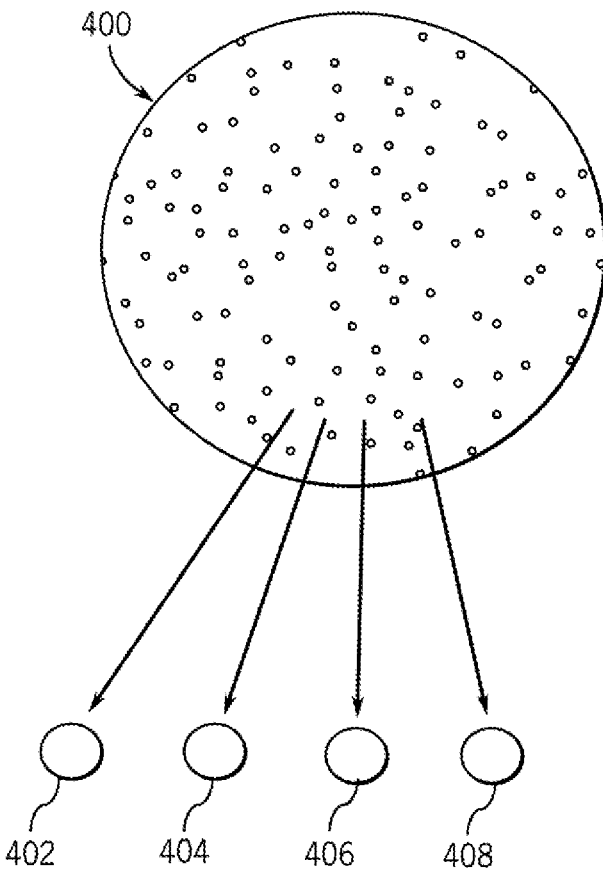
FIG. 4 illustrates one example of an effervescent mineral composition of the present technology.

FIG. 4 illustrates one example of effervescent mineral composition 400 of the present technology. As shown, the effervescent mineral composition 400 is in a spherical compressed bath additive form. Effervescent mineral composition 400 includes at least bicarbonate 402 and acid 404. Effervescent mineral composition 400 also preferably includes and at least one fat facilitator 406. The bicarbonate 402 and acid 404 may be present in a ratio of about 3:2.

Bicarbonate 402 may include at least one of sodium hydrogen carbonate and sodium carbonate.

Acid 404 may include at least one of citric acid, lactic acid, and vinegar. Lactic acid may be preferable in at least some instances.

The at least one fat facilitator 406 may include at least one fat, which may facilitate inducement of electrophoration. The at least one fat facilitator 406 may include at least one of a moisturizer, lactose, and calcium silicate.

Effervescent mineral composition 400 may also include a vaso dilator 408, such as nitric oxide.

Effervescent mineral compositions of the present technology in the form of a compressed solid or a powder. Examples of compressed solids include, but are not limited to, spheres, cylinders, squares, tablets, and other geometric shapes. Generally, the components of the composition may be combined in a dry or moistened state, compressed into a mold having the desired shape, and then dried to form the compressed solid. When activated, effervescent mineral compositions of the present technology generate carbon dioxide, and when activated effervescent mineral compositions of the present technology are applies to the target area, they result in the cutaneous application of carbon dioxide. Effervescent mineral compositions of the present technology may be activated by placing it in a bath, or otherwise applying water to form a wet active composition. Cutaneous application of carbon dioxide may be accomplished by submersing the target area in a water bath containing an activated effervescent mineral composition of the present technology, or by applying the wet active composition to the target area.

Figure 5:
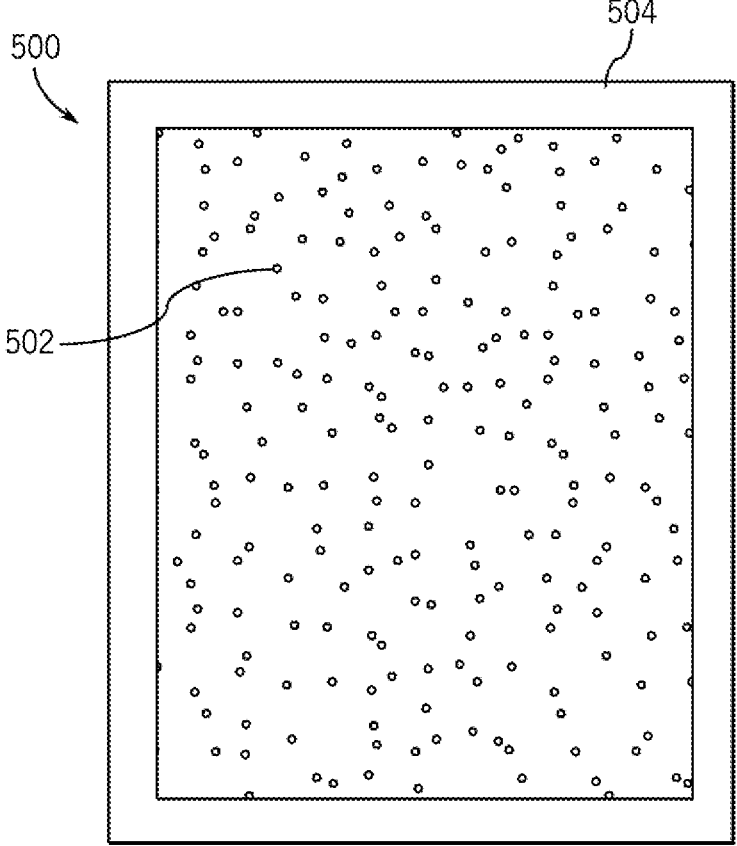
FIG. 5 illustrates one example of an effervescent mineral composition pack of the present technology.

FIG. 5 illustrates one example of an enclosed pack 500 containing an effervescent mineral composition 502 of the present technology. The enclosed pack 500 may be activated and placed on the external region of target biological tissue, such as on a patient's skin at the area of the target biological tissue. Effervescent mineral composition 502 includes at least bicarbonate 402 and acid 404, as shown in FIG. 4, and may also include at least one of the at least one fat facilitator 406, and the vaso dilator 408. The enclosed pack 500 may include a water permeable layer 504, and the effervescent mineral composition 502 within the pack may be activated by the application of water to the water permeable outer layer 504 of the enclosed pack 500.

Examples

The treatment method described herein is exemplary and it should be understood that the present technology encompasses, but is not limited to, the specific examples provided.

A. Neuropathy

One example of a treatment method of the present technology is directed to the treatment of neuropathy. The initial treatment phase of the neuropathy treatment method includes multiple therapy sessions, for example a total of twelve therapy sessions, where the therapy sessions are scheduled three times per week over a period of four weeks.

Each therapy session includes a combination of subcutaneous and cutaneous applications of carbon dioxide to the target area.

First, the clinician administers at least one subcutaneous injection of carbon dioxide at least one point in the target area. For neuropathy, the target area includes the specific location of the neuropathy, i.e., the target biological tissue, as well as surrounding tissues distal of the neuropathy. In the early therapy sessions, the subcutaneous carbon dioxide may be administered at a point within the target area distal of the target biological tissue, rather than directly at the target biological tissue, which may increase patient comfort. As the therapy progresses, the subcutaneous application of carbon dioxide may be administered progressively more proximal to the target biological tissue, or directly at the target biological tissue.

After the subcutaneous application of carbon dioxide, the clinician administers cutaneous carbon dioxide to the target area. For example, the clinician may place at least the target area of the patient in at least one water bath and add an effervescent mineral composition of the present technology. If the target area of the patient is the feet, the clinical may place each foot of the patient into a separate water bath, with a first foot in a first water bath and a second foot in a second water bath. An effervescent mineral composition of the present technology may then be added to each water bath.

Subsequent to, or simultaneously with, the cutaneous application of carbon dioxide, the clinical may administer electrical stimulation for a period of time that is from about 15 minutes to about 30 minutes, such as about 20 minutes. The nerve stimulator includes a current generator, a positive lead that is connected to the first water bath, and a negative lead that is connected to the second water bath. The current generator may generate bidirectional current with a voltage of +0 to 36V, and −0 to 36V. The current generator may further generate current having a symmetrical biphasic rectangular wave form that modulates with bursts every 5 seconds on and off.

Additionally, subsequent to the cutaneous application of carbon dioxide, the clinician may administer physical manipulation of the target area.

During the time period between scheduled therapy sessions, the clinician may instruct the patient to self-administer one or more cutaneous carbon dioxide applications. For example, the patient may self-administer a cutaneous carbon dioxide application once or twice per week, or more frequently, on days when a therapy session is not scheduled.

Once the initial treatment phase is complete, the maintenance phase may include a therapy session once per month, or once every two months, for an indefinite period of time. During the maintenance phase, the patient may self-administer cutaneous carbon dioxide once per week.

B. Neuro Muscular Skeletal

One example of a treatment method of the present technology is directed to the treatment of neuro muscular skeletal damage. The initial treatment phase of the neuro muscular skeletal treatment method includes multiple therapy sessions, for example a total between six and eight therapy sessions, where the therapy sessions are scheduled two or three times per week over a period of three weeks.

Each therapy session includes a combination of subcutaneous carbon dioxide application and physical manipulation. First, the clinician administers at least one subcutaneous injection of carbon dioxide at a point in the target area. Then, the clinician may administer physical manipulation of the target area. Each therapy session may also include application of a secondary treatment, preferably subsequent to the subcutaneous carbon dioxide application, and prior or subsequent to the physical manipulation. The secondary treatment may be electrical stimulation or extracorporeal shock wave therapy.

The initial treatment phase also includes administration of cutaneous carbon dioxide to the target area. For example, cutaneous carbon dioxide may be applied to the target biological tissue once or twice per week, or more frequently. The cutaneous carbon dioxide may be administered on the same day of, and after, a scheduled therapy session, or on days when a therapy session is not scheduled.

Once the initial treatment phase is complete, the maintenance phase may include administration of cutaneous carbon dioxide once per week, once every two weeks, or monthly, over an indefinite period of time. The maintenance phase may also include scheduled therapy sessions spaced apart in time, such as once every two or three months, or as needed.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A regenerative treatment method for treating target biological tissue within a target area of a patient, the method comprising:
administering an initial treatment phase comprising administering at least one initial phase therapy session and administering at least one initial phase personal administration,
wherein administering each initial phase therapy session includes at least:
subcutaneously applying carbon dioxide in the target area; and
simultaneously administering electrical stimulation to at least the target area and carbon dioxide to the outer surface of the skin in the target area by applying activated effervescent mineral composition to the target area, wherein the effervescent mineral composition comprises bicarbonate and an acid, by:
providing a first water bath and a second water bath, each water bath containing a volume of water and the effervescent mineral composition; and
providing a current generator having a positive lead connected to the current generator and a negative lead connected to the current generator, the positive lead being further connected to the first water bath, and the negative lead being further connected to the second water bath; and
generating a biphasic current using the current generator; and
wherein administering each initial phase personal administration consists of applying carbon dioxide to the outer surface of the skin in the target area by applying activated effervescent mineral composition to the target area, wherein the effervescent mineral composition comprises bicarbonate and an acid; and
administering a maintenance treatment phase after the initial treatment phase, the maintenance phase comprising administering at least one maintenance phase therapy session and administering at least one maintenance phase personal administration, wherein administering each maintenance phase therapy session includes at least subcutaneously applying carbon dioxide in the target area and administering each maintenance phase personal administration consists of applying carbon dioxide to the outer surface of the skin in the target area by applying activated effervescent mineral composition to the target area, wherein the effervescent mineral composition comprises bicarbonate and an acid.

2. The regenerative treatment method of claim 1, wherein administering each initial phase therapy session further comprises, subsequent to the subcutaneously applying carbon dioxide in the target area, applying carbon dioxide to the outer surface of the skin in the target area by applying activated effervescent mineral composition to the target area, wherein the effervescent mineral composition comprises bicarbonate and an acid.

3. The regenerative treatment method of claim 1, wherein administering each therapy session further comprises physically manipulating the target area subsequent to subcutaneously applying carbon dioxide in the target area.

4. The regenerative treatment method of claim 1, wherein administering each therapy session further includes administering a secondary treatment to the target area.

5. The regenerative treatment method of claim 4, wherein administering the secondary treatment comprises administering electrical stimulation to at least the target area.

6. The regenerative treatment method of claim 4, wherein administering the secondary treatment comprises administering extracorporeal shock wave therapy to at least the target area.

7. The regenerative treatment method of claim 1, wherein administering the at least one maintenance phase therapy session further includes simultaneously administering carbon dioxide to the outer surface of the skin in the target area by applying activated effervescent mineral composition to the target area, wherein the effervescent mineral composition comprises bicarbonate and an acid, and electrical stimulation to at least the target area.

8. The regenerative treatment method of claim 7, wherein the simultaneously administering carbon dioxide to the outer surface of the skin in the target area and electrical stimulation to at least the target area includes:
providing a first water bath and a second water bath, each water bath containing a volume of water and the effervescent mineral composition; and
providing a current generator having a positive lead connected to the current generator and a negative lead connected to the current generator, the positive lead being further connected to the first water bath, and the negative lead being further connected to the second water bath; and
generating a biphasic current using the current generator.

9. The regenerative treatment method of claim 1, wherein the effervescent mineral composition further comprises: at least one fat facilitator.

10. The regenerative treatment method of claim 1, wherein the bicarbonate and the acid are present in a ratio of 3:2.

11. The regenerative treatment method of claim 9, wherein the bicarbonate comprises at least one of sodium hydrogen carbonate and sodium carbonate.

12. The regenerative treatment method of claim 9, wherein the acid comprises at least one of citric acid, lactic acid, and vinegar.

13. The regenerative treatment method of claim 9, wherein the at least one fat facilitator comprises at least one of a moisturizer, lactose, and calcium silicate.

14. The regenerative treatment method of claim 9, wherein the effervescent mineral composition further comprises a vasodilator.

15. The regenerative treatment method of claim 14, wherein the vasodilator comprises nitric oxide.

16. The regenerative treatment method of claim 9, wherein the effervescent mineral composition is provided in the form of a compressed solid or a powder.

17. The regenerative treatment method of claim 9, wherein the effervescent mineral composition is provided within an enclosed pack having a water permeable layer.

18. The regenerative treatment method of claim 1, wherein generating a biphasic current using the current generator comprises generating a biphasic current with a frequency of 8 Hertz and a voltage of +0 to 36V, and −0 to 36V.

19. A regenerative treatment method for treating target biological tissue within a target area of a patient, the method comprising:

administering an initial treatment phase comprising administering at least one initial phase therapy session and administering at least one initial phase personal administration;

wherein administering each initial phase therapy session includes subcutaneously applying carbon dioxide in the target area, and subsequently administering electrical stimulation to at least the target area and simultaneously applying carbon dioxide to the outer surface of the skin in the target area by applying activated effervescent mineral composition to the target area, wherein the effervescent mineral composition comprises bicarbonate and an acid by:

providing a first water bath and a second water bath, each water bath containing a volume of water and the effervescent mineral composition; and providing a current generator having a positive lead connected to the current generator and a negative lead connected to the current generator, the positive lead being further connected to the first water bath, and the negative lead being further connected to the second water bath; and generating a biphasic current using the current generator; and wherein administering each initial phase personal administration consists of applying carbon dioxide to the outer surface of the skin in the target area by applying activated effervescent mineral composition to the outer surface of the skin in the target area, wherein the effervescent mineral composition comprises bicarbonate and an acid; and administering a maintenance treatment phase after the initial treatment phase, the maintenance phase comprising administering at least one maintenance phase therapy session and administering at least one maintenance phase personal administration;

wherein administering each maintenance phase therapy session includes subcutaneously applying carbon dioxide in the target area, and subsequently applying carbon dioxide to the outer surface of the skin in the target area by applying activated effervescent mineral composition to the outer surface of the skin in the target area, wherein the effervescent mineral composition comprises bicarbonate and an acid; and wherein administering each maintenance phase personal administration consists of applying carbon dioxide to the outer surface of the skin in the target area by applying activated effervescent mineral composition to the target area, wherein the effervescent mineral composition comprises bicarbonate and an acid.

\* \* \* \* \*